United States Patent
Wada et al.

(10) Patent No.: US 10,281,403 B2
(45) Date of Patent: May 7, 2019

(54) SENSOR CHIP AND METHOD FOR STORING SENSOR CHIP

(71) Applicant: KONICA MINOLTA, INC., Chiyoda-ku, Tokyo (JP)

(72) Inventors: Takeshi Wada, Hino (JP); Masataka Matsuo, Hachioji (JP); Naoki Hikage, Hachioji (JP); Masanori Tsukagoshi, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/429,745

(22) PCT Filed: Sep. 12, 2013

(86) PCT No.: PCT/JP2013/074664
§ 371 (c)(1),
(2) Date: Mar. 19, 2015

(87) PCT Pub. No.: WO2014/046000
PCT Pub. Date: Mar. 27, 2014

(65) Prior Publication Data
US 2015/0233834 A1  Aug. 20, 2015

(30) Foreign Application Priority Data

Sep. 19, 2012 (JP) ................................. 2012-205500

(51) Int. Cl.
*G01N 21/65* (2006.01)
*G01N 21/552* (2014.01)
*G01N 21/64* (2006.01)

(52) U.S. Cl.
CPC ......... *G01N 21/658* (2013.01); *G01N 21/553* (2013.01); *G01N 21/648* (2013.01);
(Continued)

(58) Field of Classification Search
CPC .... G01N 21/05; G01N 21/553; G01N 21/648; G01N 33/54393; G01N 33/54373; G01N 21/658; G01N 2021/651; C12Q 1/002
(Continued)

(56) References Cited

U.S. PATENT DOCUMENTS 6,104,484 A * 8/2000 Nagata ................. G01N 21/553
356/246
7,838,301 B2 * 11/2010 Muraishi .......... G01N 33/54373
356/300

(Continued)

FOREIGN PATENT DOCUMENTS

| JP | 2006308458 A | 11/2006 |
| JP | 2007085794 A | 4/2007 |

(Continued)

OTHER PUBLICATIONS

International Search Report (ISR) and Written Opinion (WO) dated Oct. 29, 2013 issued International Application No. PCT/JP2013/074664.

(Continued)

*Primary Examiner* — Isiaka O Akanbi
(74) *Attorney, Agent, or Firm* — Holtz, Holtz & Volek PC (57) ABSTRACT

A sensor chip includes: a transparent support; a metal thin film formed on one surface of the transparent support; and a reaction section in which a ligand is immobilized on an other surface of the metal thin film that is not in contact with the transparent support, wherein the sensor chip also includes a closed space-forming member which forms a closed space such that at least the reaction section is housed in the closed space, and water content in the closed space is adjusted to satisfy: X/Y<10 (μg/mm$^2$) (wherein, X represents the water content in the closed space; and Y represents the surface area of the metal thin film in the closed space).

19 Claims, 6 Drawing Sheets

(52) U.S. Cl.
CPC ............... *G01N 2021/6482* (2013.01); *G01N 2021/651* (2013.01)

(58) Field of Classification Search
USPC ................ 356/445, 246, 446; 436/518, 164
See application file for complete search history.

(56) References Cited

U.S. PATENT DOCUMENTS

| | | | |
|---|---|---|---|
| 2003/0107741 A1 | 6/2003 | Pyo et al. | |
| 2005/0200852 A1 | 9/2005 | Kimura | |
| 2006/0078985 A1* | 4/2006 | Ogura | G01N 21/05 435/287.2 |
| 2006/0109472 A1* | 5/2006 | Muraishi | G01N 21/553 356/445 |
| 2006/0159591 A1* | 7/2006 | Ohtsuka | G01N 21/05 422/88 |
| 2006/0257290 A1* | 11/2006 | Shimizu | B01L 3/0227 422/400 |
| 2007/0231924 A1* | 10/2007 | Muraishi | B01L 3/50855 436/518 |
| 2007/0273884 A1* | 11/2007 | Matsushita | G01N 21/648 356/445 |
| 2008/0007732 A1* | 1/2008 | Ja | G01N 21/6428 356/445 |
| 2009/0153869 A1 | 6/2009 | Yamashita | |
| 2010/0278696 A1 | 11/2010 | Kuruma et al. | |

FOREIGN PATENT DOCUMENTS

| | | |
|---|---|---|
| JP | 2007292585 A | 11/2007 |
| JP | 2009079963 A | 4/2009 |
| JP | 2010027748 A | 2/2010 |
| JP | 2012037477 A | 2/2012 |
| WO | 2011155179 A1 | 12/2011 |

OTHER PUBLICATIONS

Extended European Search Report dated Jun. 3, 2016, issued in counterpart European Application No. 13839543.9
European Office Action dated Jun. 19, 2017 issued in counterpart European Application No. 13839543.9.
Japanese Office Action (and English translation thereof) dated Jun. 20, 2017 issued in counterpart Japanese Application No. 2014-536797.

* cited by examiner

SENSOR CHIP AND METHOD FOR STORING SENSOR CHIP

The present U.S. patent application is a U.S. National Phase Application under 35 USC 371 of International Application No. PCT/JP2013/074664, filed on Sep. 12, 2013. This application claims priority under the Paris Convention of Japanese patent Application No. 2012-205500, filed on Sep. 19, 2013. The entirety of both the above-identified applications are incorporated herein by reference.

TECHNICAL FIELD

The present invention relates to a sensor chip in which a metal thin film is formed; and a method of storing a sensor chip. More particularly, the present invention relates to a sensor chip in which occurrence of defects such as circular protrusions can be reduced; and a method of storing a sensor chip.

BACKGROUND ART

Conventionally, when detecting an extremely small amount of substance, a variety of sample detection devices capable of detecting such a substance by application of a physical phenomenon of the substance have been used.

One example of such sample detection devices is a surface plasmon resonance device (hereinafter, referred to as "SPR device") which is made to detect, for example, an extremely small amount of analyte in a living body, by applying a phenomenon in which resonance between electrons and light in a minute region of a nanometer level or the like yields a high optical output (surface plasmon resonance (SPR) phenomenon).

Another example of the sample detection devices is a surface plasmon-field enhanced fluorescence spectroscopic measurement device (hereinafter, also referred to as "SPFS device") which is capable of detecting an analyte with higher accuracy than an SPR device based on the principle of surface plasmon-field enhanced fluorescence spectroscopy (SPFS) where surface plasmon resonance (SPR) phenomenon is applied.

In this surface plasmon-field enhanced fluorescence spectroscopy (SPFS), in a condition where attenuated total reflection (ATR) of an excitation light such as a laser light irradiated from a light source occurs at the surface of a metal thin film, a surface plasmon light (compressional wave) is generated from the surface of the metal thin film, thereby the amount of photons included in the excitation light irradiated from the light source is increased by several ten times to several hundred times so as to obtain an electric field-enhancing effect of the surface plasmon light.

In cases where such an SPR device or SPFS device is used to detect an extremely small amount of substance, it is required that a reaction section in which a ligand is immobilized on a metal thin film to be irradiated with an excitation light be washed or replaced for each sample to be detected.

Therefore, as disclosed in Patent Documents 1 to 3, by using a sensor chip having a constitution that comprises: a substrate (transparent support); a metal thin film formed on the substrate; and a reaction section in which a ligand is immobilized on the metal thin film, a sample can be easily inspected.

PRIOR ART REFERENCES

Patent Documents
  [Patent Document 1] JP-A-2010-27748
  [Patent Document 2] JP-A-2009-79963
  [Patent Document 3] JP-A-2006-308458

SUMMARY OF THE INVENTION

Problems to be Solved by the Invention

However, particularly when detecting an extremely small amount of substance using an SPR device or an SPFS device, it is required to suppress the measurement variance to an extremely low level. Thus, a reduction in the assay performance of a ligand-immobilized sensor chip used in these devices can be fatal in some cases.

Figure 6:
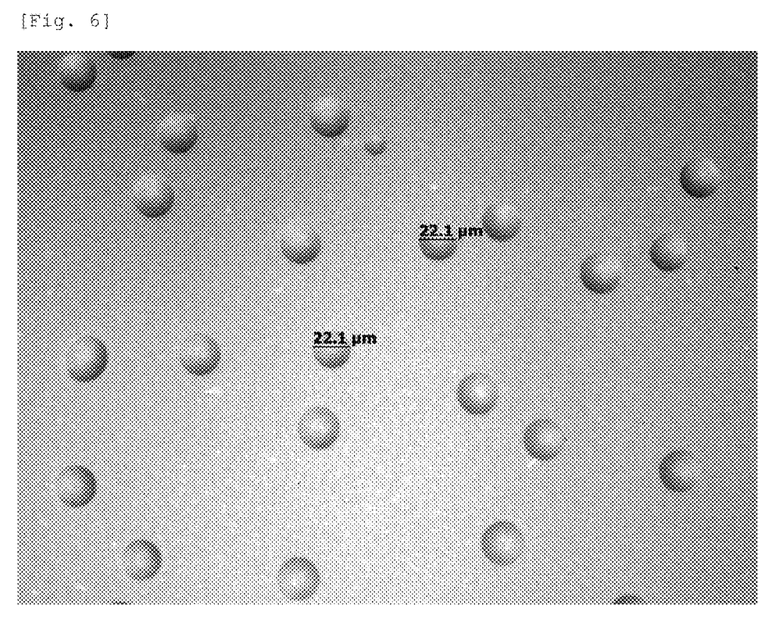
FIG. 6 is a micrograph showing circular protrusion defects generated on a metal thin film of a sensor chip.

The present inventors intensively studied suppression of a reduction in the assay performance of a sensor chip and discovered that, when a sensor chip is stored in a high-humidity condition, water or the like, depending on various storage environment and the like of the sensor chip, for example, as shown in FIG. 6, a defect such as formation of circular protrusions may occur on a metal thin film of the sensor chip, and it has thus come to understand that such a defect can cause a reduction in the assay performance of a sensor chip used for detecting an extremely small amount of substance.

In view of the above-described problems, an object of the present invention is to provide: a sensor chip in which occurrence of defects on a metal thin film, such as circular protrusions, can be reduced and a reduction in the assay performance of the sensor chip caused by such defects can be thereby suppressed; and a method of storing a sensor chip.

Technical Solution

The present invention was made to solve the above-described problems in the prior art, and the sensor chip of the present invention is characterized by comprising: a transparent support; a metal thin film formed on one surface of the transparent support; and a reaction section in which a ligand is immobilized on the other surface of the metal thin film that is not in contact with the transparent support, wherein the sensor chip also comprises a closed space-forming member which forms a closed space such that at least the reaction section is housed in the closed space, and the water content in the closed space is adjusted such that the following Formula (1) is satisfied:

$$X/Y < 10 \ (\mu g/mm^2) \tag{1}$$

(wherein, X represents the water content in the closed space; and Y represents the surface area of the metal thin film in the closed space).

Here, the closed space can be formed by the transparent support and the closed space-forming member.

Advantageous Effects of Invention

According to the present invention, occurrence of defects on a metal thin film formed on a sensor chip, such as circular protrusions, can be reduced, so that a reduction in the assay performance of the sensor chip caused by such defects can be suppressed.

DESCRIPTION OF EMBODIMENTS

Embodiments (examples) of the present invention will now be described in more detail based on the drawings.

1. Constitution of Sensor Chip

Figure 1:
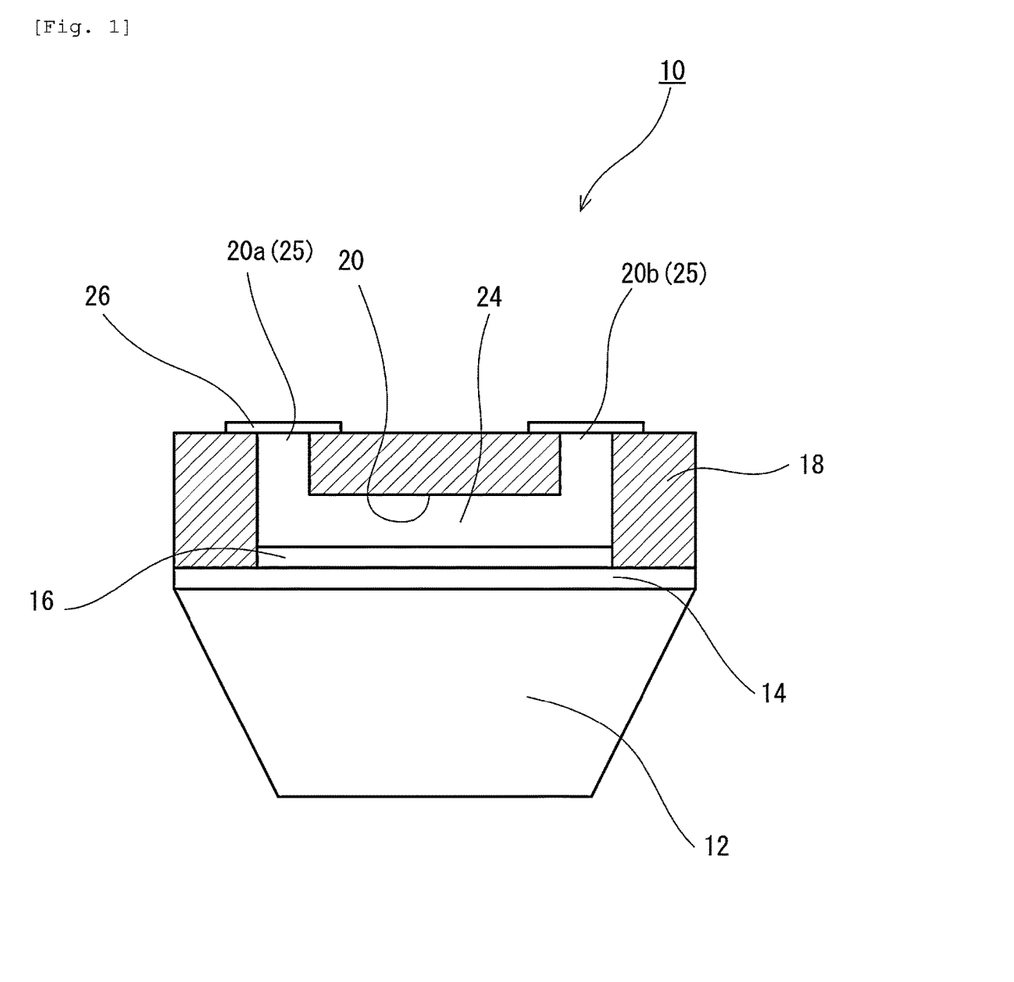
FIG. 1 is a schematic structural view for illustrating the constitution of a sensor chip according to one example of the present invention.

FIG. 1 is a schematic structural view for illustrating the constitution of a sensor chip according to one example of the present invention.

A sensor chip 10 shown in FIG. 1 comprises: a prism-shaped transparent support 12 whose vertical cross-section has a substantially trapezoidal shape; a metal thin film 14 formed on one surface of the transparent support 12; and a reaction section 16 in which a ligand is immobilized on the other surface of the metal thin film 14 that is not in contact with the transparent support 12.

The transparent support 12 is not particularly restricted as long as it has translucency; however, it is desired that the transparent support 12 have a refractive index, n, of at least 1.4 or higher, preferably 1.5 or higher. The "translucency" of the transparent support 12 means that, for example, an excitation light irradiated from a light source of an SPR device or SPFS device can at least transmit through the transparent support 12, and the transparent support 12 is not required to allow light of all wavelengths to transmit therethrough.

As the material of such transparent support 12, for example, inorganic optical materials such as synthetic quartz and glass; polyesters such as polyethylene terephthalate (PET) and polyethylene naphthalate; polyolefins such as polyethylene (PE) and polypropylene (PP); polycyclic olefins such as cyclic olefin copolymers (COC) and cyclic olefin polymers (COP); vinyl-based resins such as polyvinyl chloride and polyvinylidene chloride; polystyrene; polyether ether ketone (PEEK); polysulfone (PSF); polyether sulfone (PES); polycarbonate (PC); polyamide; polyimide; acrylic resins; and triacetyl cellulose (TAC) can be used.

Further, although the prism-shaped transparent support 12 whose vertical cross-section has a substantially trapezoidal shape is used in the sensor chip 10 of this example, the transparent support 12 can also be in the form of, for example, a prism whose vertical cross-sectional shape is triangular (so-called triangular prism), semi-circular or semi-elliptical, or a flexible film.

In order to improve the interlayer adhesion between the transparent support 12 and the metal thin film 14, it is preferred that, prior to formation of the metal thin film 14, the surface of the transparent support 12 be subjected to, for example, a washing treatment with an acid or plasma.

The washing treatment with an acid can be carried out by, for example, immersing the transparent support 12 in 0.001 to 1N hydrochloric acid for 1 to 3 hours. The washing treatment with plasma can be carried out by, for example, immersing the transparent support 12 in a plasma dry cleaner (PDC200, manufactured by Yamato Scientific Co., Ltd.) for 0.1 to 30 minutes.

The material of the metal thin film 14 is also not particularly restricted, and the metal thin film 14 is preferably made of at least one metal selected from the group consisting of gold, silver, aluminum, copper and platinum. The metal thin film 14 is more preferably made of gold, or may be composed of an alloy of these metals.

In cases where a glass is used as the transparent support 12, in order to firmly adhering the transparent support 12 and the metal thin film 14, it is preferred that a thin film (undercoat thin film) of chromium, nickel-chromium alloy, titanium or the like be formed on the surface of the transparent support 12 and the metal thin film 14 be formed on the surface of this undercoat thin film.

The method of forming such an undercoat thin film and the metal thin film 14 on the transparent support 12 is not particularly restricted, and examples thereof include a sputtering method, a vapor deposition method (such as resistance heating vapor deposition or electron beam vapor deposition), an electrolytic plating method and an electroless plating method. It is preferred to employ a sputtering method or a vapor deposition method because the thin film-forming conditions can be easily adjusted.

The thickness of the metal thin film 14 is not particularly restricted; however, it is preferably in a range of 5 to 500 nm when the metal thin film 14 is made of gold, silver, aluminum, copper, platinum or an alloy of these metals. The thickness of the undercoat thin film is desirably in a range of 1 to 20 nm.

From the standpoint of the electric field-enhancing effect, the thickness of the metal thin film 14 is more preferably in a range of 20 to 70 nm (gold), 20 to 70 nm (silver), 10 to 50 nm (aluminum), 20 to 70 nm (copper), 20 to 70 nm (platinum) or 10 to 70 nm (an alloy of these metals), and the thickness of the undercoat thin film is desirably in a range of 1 to 3 nm when it is made of chromium.

The term "ligand" used herein refers to a molecule or a molecular fragment that is capable of specifically recognizing (or being recognized by) and binding to an analyte contained in a sample. Such a "molecule" or "molecular fragment" is not particularly restricted as long as it is, for example, a nucleic acid (such as DNA, RNA, polynucleotide, oligonucleotide or PNA (peptide nucleic acid), which may be single-stranded or double stranded, or a nucleoside, nucleotide or modified molecule thereof), a protein (such as polypeptide or oligopeptide), an amino acid (including a modified amino acid), a saccharide (such as oligosaccharide, polysaccharide or sugar chain), a lipid, or a modified molecule or a complex of these substances.

Examples of the "protein" include antibodies, specifically anti-α fetoprotein (AFP) monoclonal antibodies (available from, for example, Japan Clinical Laboratories, Inc.), anti-carcinoembryonic antigen (CEA) monoclonal antibodies, anti-CA19-9 monoclonal antibodies and anti-PSA monoclonal antibodies. In the present invention, the term "antibody" encompasses polyclonal antibodies, monoclonal antibodies, antibodies obtained by gene recombination, and antibody fragments.

As a method of immobilizing the ligand, a known method disclosed in, for example, JP-A-2009-79963 or JP-A-2012-37477 can be employed. Examples thereof include (1) a method in which a reactive polymer layer comprising a reactive polymer having a functional group(s) such as a hydroxy group, an amino group, a carboxyl group and/or an isocyanate group (preferably a hydroxy group and a carboxyl group) is formed on the surface of a transparent support and a chemical bond is formed by reaction between the various functional groups of the reactive polymer and a functional group of a ligand; and (2) a method in which a layer comprising a compound having a sensitive reactive group (such as a silane coupling agent) is formed on the surface of a transparent support and a ligand is immobilized via the compound.

Examples of the reactive polymer include carboxymethyl dextran (CMD), polyethylene glycol, iminodiacetic acid derivatives (such as (N-5-amino-1-carboxypentyl)iminodiacetic acid), biotin-avidin, biotin-streptavidin, protein A and protein G.

The "silane coupling agent" is not particularly restricted as long as it has an ethoxy group (or a methoxy group) yielding a silanol group (Si—OH) by hydrolysis and a reactive group such as an amino group, a glycidyl group or a carboxyl group at the other end, and a conventionally known silane coupling agent can be used.

The sensor chip 10 of this example also comprises a flow path member 18 as a reaction space-forming member for introducing an analyte-containing sample solution to the reaction section 16 of the sensor chip 10. As shown in FIG. 1, the flow path member 18 is constituted in such a manner that a flow path 20 is formed by the transparent support 12 and the flow path member 18 and the sample solution is fed to the reaction section 16.

That is, a reaction space 24 is formed above the reaction section 16 of the flow path 20 and, by allowing the sample solution to flow in this reaction space 24, the analyte contained in the sample solution reacts with the ligand of the reaction section 16 and the analyte is consequently captured by the ligand.

The method of allowing the sample solution to flow in the flow path 20 is not particularly restricted. A pump (not shown) may be connected to both ends, 20a and 20b, of the flow path 20 so as to circulate the sample solution in one direction or the sample solution may be fed by injection from the end 20a of the flow path 20 using a pipette, or the sample solution may be allowed to flow reciprocally in the reaction section 16 by sucking and discharging the sample solution using a pipette while injecting the sample solution.

Particularly, by allowing the sample solution to flow reciprocally in the reaction section 16, even when the sample solution is in a small amount, the efficiency of the reaction between the analyte and the ligand is increased and the analyte detection accuracy can be thereby improved.

The reaction section 16 does not have to completely cover the metal thin film 14 facing the reaction space 24. Particularly, by reducing the area of the reaction section 16, the analyte contained in the sample solution is captured at a high density.

Figure 2:
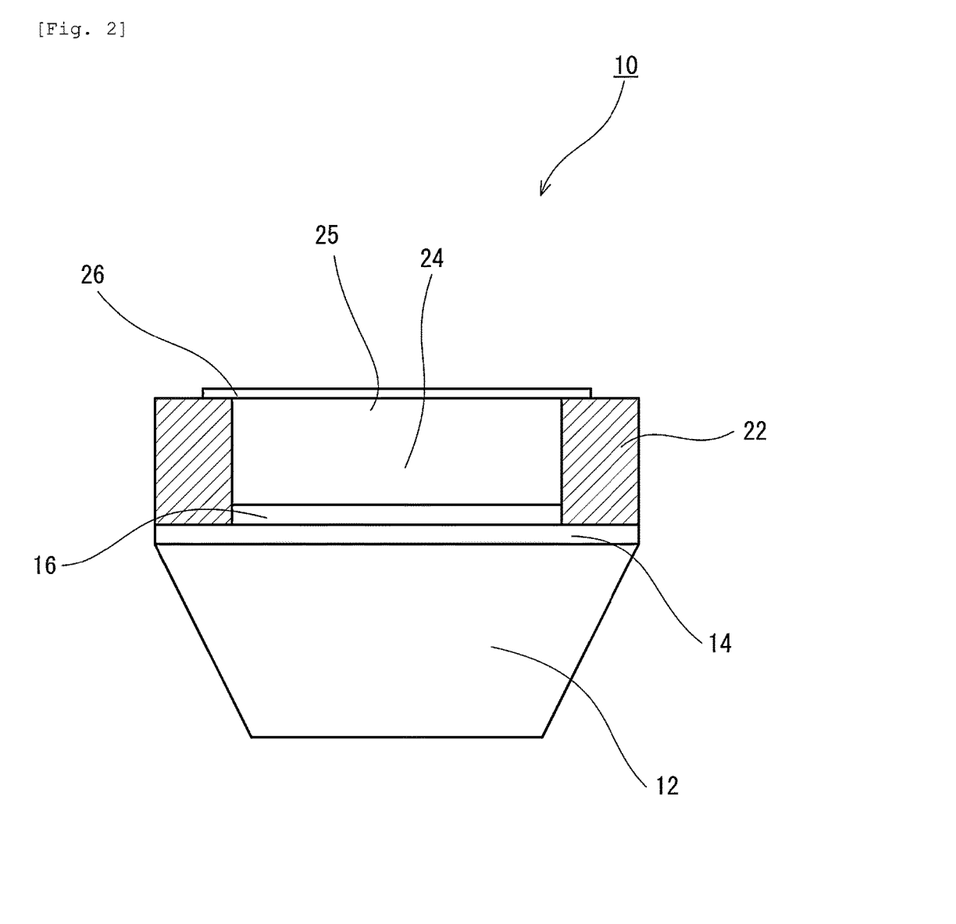
FIG. 2 is a schematic structural view showing a modification example of the sensor chip of FIG. 1, where a well member is used as a reaction space-forming member.

In this example, the flow path member 18 is used as the reaction space-forming member; however, the reaction space-forming member is not particularly restricted thereto as long as it is capable of temporarily retaining the analyte-containing sample solution on the reaction section 16 or transferring the analyte-containing sample solution to the reaction section 16. For example, as shown in FIG. 2, the reaction space-forming member may be a well member 22, which constitutes a wall surrounding the reaction section 16 to form the reaction space 24.

The materials of these reaction space-forming members (the flow path member 18 and the well member 22) are not particularly restricted and, for example, a variety of inorganic materials such as glass and ceramics, natural polymers and synthetic polymers can be used.

Further, on the opening side 25 of the reaction space-forming member (the flow path member 18 or the well member 22), a closed space-forming member 26 is arranged so as to make the reaction space 24 a closed space.

That is, a closed space is formed by the transparent support 12, the reaction space-forming member (the flow path member 18 or the well member 22) and the closed space-forming member 26.

Further, the water content in this closed space is adjusted such that the water content in the closed space, X, and the area of the metal thin film 14 in the closed space, Y, satisfy the following Formula (1).

$$X/Y < 10 \; (\mu g/mm^2) \tag{1}$$

By adjusting the water content in the closed space in this manner, even when the sensor chip 10 is stored for an extended period of time, defects such as circular protrusions do not occur on the metal thin film 14 and a reduction in the assay performance of the sensor chip 10 can be suppressed.

The closed space-forming member 26 is not particularly restricted as long as it hardly causes a change in the water content of the closed space and, for example, a high moisture barrier resin film such as a polyvinylidene chloride film, a polypropylene film or a polyacrylonitrile film, a multilayer film comprising these resin films, or a composite film constituted by a metal thin film such as an aluminum foil or a gold thin film and a resin film can be used as the closed space-forming member 26.

Further, the closed space-forming member 26 is not restricted to a film and, for example, a variety of inorganic materials such as glass and ceramics, natural polymers and synthetic polymers may be molded into a plate form to be used as the closed space-forming member 26.

Figure 3:
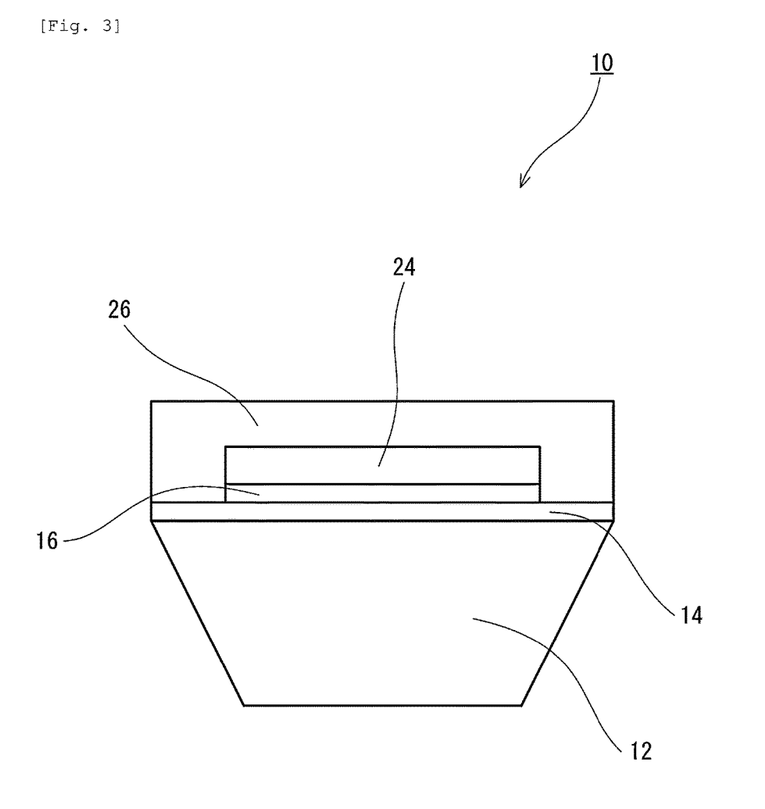
FIG. 3 is a schematic structural view showing a modification example of the sensor chip of FIG. 1, where a closed space is formed by a transparent support and a closed space-forming member.

In cases where the sensor chip 10 is constituted without any reaction space-forming member, for example, as shown in FIG. 3, the shape of the closed space-forming member 26 can be modified such that a closed space is formed by the transparent support 12 and the closed space-forming member 26.

Figure 4:
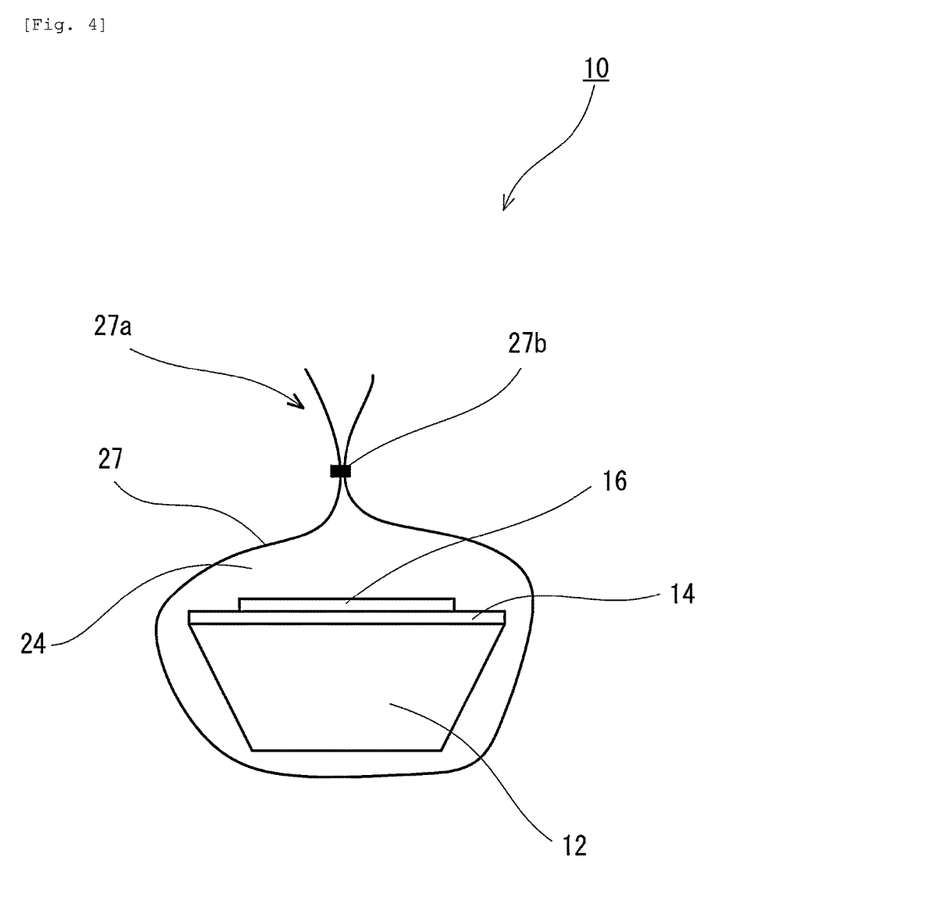
FIG. 4 is a schematic structural view showing a modification example of the sensor chip of FIG. 1, where a closed space is formed by a packaging material that is a closed space-forming member.

Further, in cases where the closed space 24 is formed by the closed space-forming member 26 alone, for example, as shown in FIG. 4, the sensor chip 10 is enclosed in a packaging material 27, which is a closed space-forming member, and a mouth 27a of the packaging material 27 can be sealed with a seal member 27b.

The method of adjusting the water content in the closed space such that the Formula (1) is satisfied is not particularly restricted and, for example, a drying method such as hot-air drying, vacuum drying, steam drying or suction drying can be selected as appropriate in accordance with the shape and the like of the reaction space-forming member.

2. Method of Using Sensor Chip

The sensor chip 10 having the above-described constitution is used in, for example, optical sample detection devices such as SPR devices and SPFS devices.

Figure 5:
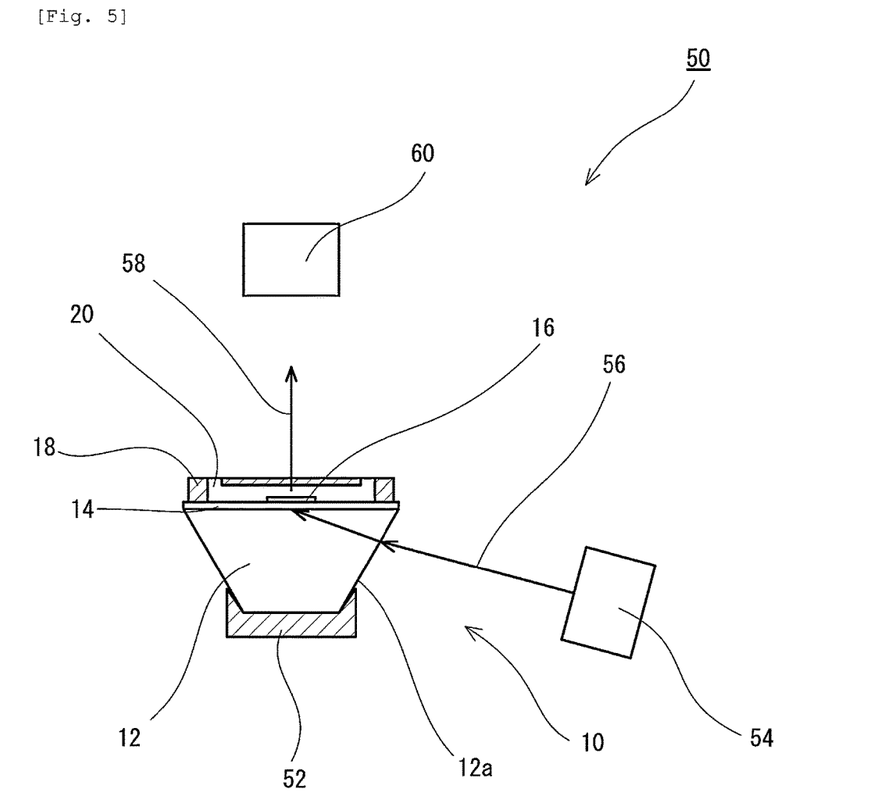
FIG. 5 is a schematic structural view for illustrating, as one example of a method of using the sensor chip of FIG. 1, a configuration in which a sensor chip 10 is used in an SPFS device.

FIG. 5 is a schematic structural view for illustrating, as one example of a method of using the sensor chip of FIG. 1, a configuration in which the sensor chip 10 is used in an SPFS device.

As shown in FIG. 5, in an SPFS device 50 of this example, the sensor chip 10 is mounted on a sensor chip-mounting part 52 arranged in the SPFS device 50. In this example, a prism-shaped transparent support 12 whose vertical cross-section has a substantially trapezoidal shape is used as the transparent support 12; however, when the transparent support 12 is in the form of a flexible film, the sensor chip 10 can be immobilized on the upper surface of a prism-shaped dielectric member mounted in the sensor chip-mounting part 52.

Further, on the side of a lower side surface 12a of the sensor chip 10, as shown in FIG. 5, a light source 54 is arranged such that an excitation light 56 emitted therefrom enters the side surface 12a of the transparent support 12 from the lower side of the transparent support 12 (or dielectric member) of the sensor chip 10 and is irradiated via the transparent support 12 toward the metal thin film 14 formed on the upper surface of the transparent support 12.

The light source 54 comprises an incident angle-adjusting means (not shown) which enables to appropriately change the incident angle of the excitation light 56 irradiated from the light source 54 with respect to the metal thin film 14, so that the incident angle of the excitation light 56 can be appropriately changed when performing SPFS measurement.

Further, as described below, above the sensor chip 10, a light detection means 60, which receives fluorescent light 58 that is emitted from an analyte-labeling fluorescent substance excited by surface plasmon light (compression wave) generated on the metal thin film 14, is arranged.

In the SPFS device 50 having the above-described constitution, the closed space-forming member 26 is removed first and an appropriate amount of analyte-containing sample solution is then allowed to flow in the flow path 20 for a prescribed time. As a result, the analyte is captured by the ligand immobilized on the reaction section 16 arranged on the metal thin film 14.

Here, in cases where a film is used as the closed space-forming member 26, without removing the closed space-forming member 26, the sample solution may be fed to the flow path 20 by, for example, inserting the tip of a pipette or the like into the film to penetrate the closed space-forming member 26.

Next, an appropriate amount of a fluorescent substance solution containing a fluorescent substance for labeling the analyte is allowed to flow in the flow path 20 for a prescribed time. As a result, the analyte captured by the ligand on the reaction section 16 is labeled with the fluorescent substance.

In this manner, the analyte labeled with the fluorescent substance is in a state of being captured in the reaction section 16 of the sensor chip 10. In this state, by irradiating the metal thin film 14 of the sensor chip 10 with the excitation light 56 emitted from the light source 54 via the transparent support 12 and allowing the light detection means 60 to receive the fluorescent light 58, the amount of fluorescence can be determined by SPFS measurement.

Then, for example, by comparing the thus determined amount of fluorescence with a calibration curve prepared in advance that pertains to the analyte concentration and the amount of fluorescence, the total amount of the analyte contained in the sample solution (analyte concentration) can be calculated.

EXAMPLES

Using the above-described sensor chip 10, the presence or absence of a defect in the metal thin film 14 and the assay performance of the sensor chip 10 were verified when the sensor chip 10 was stored with change in the water content of the closed space in each case.

The verification of the presence or absence of a defect in the metal thin film 14 was performed by observing the surface condition of the metal thin film 14 under a light microscope. Further, the water content in the closed space was measured using a Karl-Fisher moisture meter for a sensor chip that was prepared separately from the sensor chip used for the verification of assay performance by the completely same method.

The assay performance was verified by the following procedure.

First, an AFP solution (2.0 mg/mL solution, Acris Antibodies GmbH) diluted with PBS buffer (pH 7.4) to an AFP concentration of 0.1 ng/mL was allowed to flow in the flow path 20 for 20 minutes at a flow rate of 500 µL/min.

Next, 1% BSA-PBS buffer solution (pH 7.4) containing an Alexa Fluor 647-labeled anti-AFP monoclonal antibody as a labeled antibody at a concentration of 2.5 µg/mL was allowed to flow for 20 minutes at a flow rate of 500 µL/min. Then, as a washing step, a 0.005% Tween 20-containing TBS solution (pH 7.4) was allowed to flow for 10 minutes at a flow rate of 500 µL/min.

After the washing step, with the flow path being filled with PBS buffer (pH 7.4), a laser light (640 nm, 40 µW) was irradiated via a prism from the back side of a plasmon excitation sensor and the amount of fluorescence emitted from the sensor surface was measured using a CCD. This measurement value was defined as "assay signal".

On another front, for other sensor chip 10, the amount of fluorescence was measured by the same procedure as described above except that PBS buffer (pH 7.4) containing absolutely no AFP (0 ng/mL) was used as the solution that was allowed to flow first, and the thus obtained measurement value was defined as "blank signal". Using the blank signal and the assay signal, the value of S/N was calculated using the following equation.

$$S/N = |(\text{assay signal})| / |(\text{blank signal})|$$

The conditions of the respective Examples and Comparative Examples were as follows. The obtained results are shown in Table 1.

In Example 1, a cycloolefin polymer resin (ZEON Corporation, ZEONEX (registered trademark)) was used as the material of the transparent support 12 and the water content in the closed space was adjusted to be 0.01 µg/mm$^2$.

In Example 2, a cycloolefin polymer resin (ZEON Corporation, ZEONEX (registered trademark)) was used as the material of the transparent support 12 and the water content in the closed space was adjusted to be 0.25 µg/mm$^2$.

In Example 3, a cycloolefin polymer resin (ZEON Corporation, ZEONEX (registered trademark)) was used as the material of the transparent support 12 and the water content in the closed space was adjusted to be 1.1 µg/mm$^2$.

In Example 4, a cycloolefin polymer resin (ZEON Corporation, ZEONEX (registered trademark)) was used as the material of the transparent support 12 and the water content in the closed space was adjusted to be 9.5 µg/mm$^2$.

In Example 5, a polymethyl methacrylate resin (PMMA) was used as the material of the transparent support 12 and the water content in the closed space was adjusted to be 6.4 µg/mm$^2$.

In Example 6, a synthetic quartz glass (BK7) was used as the material of the transparent support 12 and the water content in the closed space was adjusted to be 7.7 µg/mm$^2$.

In Comparative Example 1, a cycloolefin polymer resin (E48R (ZEON Corporation, ZEONEX (registered trademark))) was used as the material of the transparent support 12 and the water content in the closed space was adjusted to be 12 µg/mm².

In Comparative Example 2, a cycloolefin polymer resin (ZEON Corporation, ZEONEX (registered trademark)) was used as the material of the transparent support 12 and the sensor chip 10 was stored without the closed space-forming member 26 being arranged.

In Comparative Example 3, a polymethyl methacrylate resin (PMMA) was used as the material of the transparent support 12 and the water content in the closed space was adjusted to be 14.5 µg/mm².

In Comparative Example 4, a synthetic quartz glass (BK7) was used as the material of the transparent support 12 and the water content in the closed space was adjusted to be 13.5 µg/mm².

TABLE 1

|  | Conditions | | | Storage results | |
|---|---|---|---|---|---|
|  | Material | Closed condition | Water content (µg/mm2) | Defect of metal thin film | Assay performance |
| Example 1 | E48R | OK | 0.01 | absent | ○ |
| Example 2 | E48R | OK | 0.25 | absent | ○ |
| Example 3 | E48R | OK | 1.1 | absent | ○ |
| Example 4 | E48R | OK | 9.5 | absent | ○ |
| Comparative Example 1 | E48R | OK | 12 | present | Δ~○ |
| Comparative Example 2 | E48R | NG | — | present | x |
| Example 5 | PMMA | OK | 6.4 | absent | ○ |
| Comparative Example 3 | PMMA | OK | 14.5 | present | Δ~○ |
| Example 6 | BK7 | OK | 7.7 | absent | ○ |
| Comparative Example 4 | BK7 | OK | 13.5 | present | Δ~○ |

DESCRIPTION OF SYMBOLS

10: sensor chip
12: transparent support
12a: side surface
14: metal thin film
16: reaction section
18: flow path member
20: flow path
20a: end
20b: end
22: well member
24: reaction space
25: opening side
26: closed space-forming member
27: packaging material
27a: mouth
27b: seal member
50: SPFS device
52: sensor chip-mounting part
54: light source
56: excitation light
58: fluorescent light
60: light detection means
○ in [Table 1]: excellent Assay performance
Δ~○ in [Table 1]: good Assay performance
X in [Table 1]: poor Assay performance

The invention claimed is:

1. A sensor chip, comprising:
a transparent support;
a metal thin film formed on one surface of the transparent support;
a reaction section in which a ligand is immobilized on a surface of the metal thin film that is not in contact with the transparent support; and
a closed space-forming member which forms a closed space such that at least the reaction section is housed in the closed space, wherein the closed space-forming member comprises a moisture barrier material and has a structure such that a water content in the closed space is maintained,
wherein the water content in the closed space is adjusted such that the following Formula (1) is satisfied:

$$X/Y<10 \; (\mu g/mm^2) \qquad (1)$$

where:
X represents the water content in the closed space; and
Y represents a surface area of the metal thin film in the closed space,
wherein the closed space is formed by the transparent support and the closed space-forming member, and
wherein the closed space-forming member comprises a top cover and a plurality of side walls which, together with the transparent support, enclose the closed space.

2. The sensor chip according to claim 1, wherein the closed space-forming member comprises a polyvinylidene chloride film, a polypropylene film, or a polyacrylonitrile film.

3. The sensor chip according to claim 1, wherein the closed space-forming member comprises a multilayer film including a plurality of resin films.

4. The sensor chip according to claim 1, wherein the closed space-forming member comprises a composite film including a metal thin film and a resin film.

5. The sensor chip according to claim 1, wherein the closed space-forming member comprises a glass or ceramic plate.

6. The sensor chip according to claim 1, wherein the side walls of the closed space-forming member contact the metal thin film formed on the transparent substrate.

7. A method of storing a sensor chip which comprises: a transparent support; a metal thin film formed on one surface of the transparent support; and a reaction section in which a ligand is immobilized on a surface of the metal thin film that is not in contact with the transparent support, the method comprising:
providing a closed-space forming member on the transparent support to form a closed space such that at least the reaction section is housed in the closed space, wherein the closed space-forming member comprises a moisture barrier material and has a structure such that a water content in the closed space is maintained; and
adjusting the water content in the closed space such that the following Formula (1) is satisfied:

$$X/Y<10 \; (\mu g/mm^2) \qquad (1)$$

where:
X represents the water content in the closed space; and
Y represents a surface area of the metal thin film in the closed space,
wherein the closed space is formed by the transparent support and the closed space-forming member, and wherein the closed space-forming member comprises a top cover and a plurality of side walls which, together with the transparent support, enclose the closed space.

8. The method according to claim 7, wherein the closed space-forming member comprises a polyvinylidene chloride film, a polypropylene film, or a polyacrylonitrile film.

9. The method according to claim 7, wherein the closed space-forming member comprises a multilayer film including a plurality of resin films.

10. The method according to claim 7, wherein the closed space-forming member comprises a composite film including a metal thin film and a resin film.

11. The method according to claim 7, wherein the closed space-forming member comprises a glass or ceramic plate.

12. The method according to claim 7, wherein the closed-space forming member is provided on the transparent support such that the side walls of the closed space-forming member contact the metal thin film formed on the transparent substrate.

13. A sensor chip, comprising:
a transparent support;
a metal thin film formed on one surface of the transparent support;
a reaction section in which a ligand is immobilized on a surface of the metal thin film that is not in contact with the transparent support;
a reaction space-forming member which contacts the metal thin film, forms a reaction space above the reaction section, and has at least one opening for a sample solution; and
a closed space-forming member which contacts the reaction space-forming member and closes the at least one opening in the reaction space forming member, to form a closed space in which at least the reaction section is housed,
wherein the closed space-forming member comprises a high moisture barrier film or a high moisture barrier plate, such that a water content in the closed space is maintained, and
wherein the water content in the closed space is adjusted such that the following Formula (1) is satisfied:

$$X/Y < 10 \ (\mu g/mm^2) \qquad (1)$$

where:
X represents the water content in the closed space; and
Y represents a surface area of the metal thin film in the closed space.

14. The sensor chip according to claim 13, wherein the reaction space-forming member comprises a flow path member which has a plurality of openings and which, together with the transparent substrate, forms a flow path; and
wherein the closed space-forming member contacts the flow path member and closes the plurality of openings in the flow path member.

15. The sensor chip according to claim 13, wherein the reaction space-forming member comprises a well member which has an opening; and
wherein the closed space-forming member contacts the well member and closes the plurality of openings in the well member.

16. The sensor chip according to claim 13, wherein the closed space-forming member comprises a polyvinylidene chloride film, a polypropylene film, or a polyacrylonitrile film.

17. The sensor chip according to claim 13, wherein the closed space-forming member comprises a multilayer film including a plurality of resin films.

18. The sensor chip according to claim 13, wherein the closed space-forming member comprises a composite film including a metal thin film and a resin film.

19. The sensor chip according to claim 13, wherein the closed space-forming member comprises a glass or ceramic plate.

* * * * *